United States Patent
Brehove

(10) Patent No.: US 6,878,365 B2
(45) Date of Patent: Apr. 12, 2005

(54) TOPICAL APPLICATION FOR TREATING TOENAIL FUNGUS

(76) Inventor: James Edward Brehove, 11 Cliff Ct., Succasunna, NJ (US) 07876

(*) Notice: Subject to any disclaimer, the term of this patent is extended or adjusted under 35 U.S.C. 154(b) by 283 days.

(21) Appl. No.: 10/077,521

(22) Filed: Feb. 15, 2002

(65) Prior Publication Data

US 2002/0165121 A1 Nov. 7, 2002

Related U.S. Application Data

(60) Provisional application No. 60/274,391, filed on Mar. 10, 2001.

(51) Int. Cl.$^7$ .............. A61K 7/04; A61K 6/00; A01N 59/00; A01N 59/14; A01N 55/02
(52) U.S. Cl. .......... 424/61; 424/401; 424/600; 424/657; 556/7; 514/947; 514/492
(58) Field of Search ............ 424/400, 401, 424/61, 78.02, 78.03, 78.08, 600, 657; 514/492, 947; 556/7

(56) References Cited

U.S. PATENT DOCUMENTS

| | | | |
|---|---|---|---|
| 2,741,548 A | 4/1956 | Darling et al. ........ 44/63 |
| 3,009,799 A | 11/1961 | Dykstra ............. 52/5 |
| 3,189,637 A | 6/1965 | Bengelsdorf et al. ... 260/462 |
| 3,510,554 A | 5/1970 | Balsiger et al. ....... 424/61 |
| 3,877,890 A | 4/1975 | Maisey et al. ........ 44/76 |
| 4,285,934 A | 8/1981 | Tinnell .............. 424/148 |
| 4,608,440 A | * 8/1986 | Saischek et al. ....... 504/152 |
| 4,718,919 A | 1/1988 | DeLue et al. ......... 44/76 |
| 4,742,044 A | 5/1988 | Boden ............... 512/12 |
| 5,346,692 A | * 9/1994 | Wohlrab et al. ....... 424/61 |
| 5,391,367 A | 2/1995 | De Vincentis et al. ... 424/61 |
| 5,464,610 A | 11/1995 | Hayes, Jr. et al. ..... 424/61 |
| 5,487,776 A | 1/1996 | Nimni ............... 106/18.35 |
| 5,696,105 A | 12/1997 | Hackler ............. 514/172 |
| 5,760,052 A | 6/1998 | Peacock ............. 514/297 |
| 5,840,283 A | 11/1998 | Sorenson et al. ...... 424/61 |
| 5,866,105 A | 2/1999 | Richter et al. ....... 424/61 |
| 5,874,476 A | * 2/1999 | Hsu et al. ........... 514/640 |
| 5,916,545 A | 6/1999 | Burnett et al. ....... 424/61 |
| 5,972,317 A | * 10/1999 | Sorenson et al. ...... 424/61 |
| 6,022,549 A | 2/2000 | Dyer ................ 424/401 |

OTHER PUBLICATIONS

Lewis Sr., R.J., "Boron Compounds, Safety Profile", Sax's Dangerous Properties of Industrial Materials, Tenth Edition, John Wiley & Sons, New York, 546 (2000).
BIOBOR JF® . . . Material Safety Data Sheet, Hammonds Fuel Additives Inc., Houston, TX, Jan. 1, 2000.

* cited by examiner

Primary Examiner—Michael G. Hartley
Assistant Examiner—Sharmila S. Gollamudi
(74) Attorney, Agent, or Firm—Ernest D. Buff & Associates, LLC; Ernest D. Buff; Mark J. Halvorson

(57) ABSTRACT

A topical applications is used to treat and prevent the spread of nail infections or onychomycosis caused by bacteria, fungi and other pathogens. The topical application has a composition that comprises, as an active ingredient, at least one species selected from the group consisting of 2,2'-(alkyldioxy)bis-(alkyl-1,3,2-dioxaborinane) and 2,2'-oxybis (alkyl-1,3,2-dioxaborinane). More specifically, the composition comprises, as an active ingredient, at least one member selected from the group consisting of 2,2'-(1-methyltrimethylenedioxy)bis-(4-methyl-1,3,2-dioxaborinane) and 2,2'-oxybis(4,4,6-trimethyl-1,3,2-dioxaborinane).

2 Claims, No Drawings

TOPICAL APPLICATION FOR TREATING TOENAIL FUNGUS

CROSS-REFERENCE TO RELATED APPLICATIONS

This application claims the benefit of U.S. Provisional Patent Application No. 60/274,391, filed Mar. 10, 2001, entitled "Topical Application For Treating Toenail Fungus".

BACKGROUND OF THE INVENTION

1. Field of the Invention

This invention relates to the treatment of human fingernails and toenails; and more particularly, to topical applications and methods to cure or prevent the spread of nail infections, such as onychomycosis, caused by bacteria, fungi and other pathogens.

2. Description of the Related Art

Onychomycosis is a nail disease of the toes and fingers typically caused by the organisms *Candida albicans, Trichophyton mentagrophytes, Trichophyton rubrum,* or *Epidermpophyton floccusum.* The nails become thickened and lusterless, and debris accumulates under the free edge. Nail plates becomes separated and the nails may be destroyed. It is acknowledged that the therapy of onychomycosis is difficult and protracted. Oral therapy with anitmycotics requires months of administration and must be closely monitored for side effects.

Topical compositions have long been used with the objective of treating onychomycosis. Representative compositions used for this purpose are disclosed by U.S. Pat. Nos. 5,346,692; 5,391,367; 5,464,610; 5,487,776; 5,696,105; 5,760,052; 5,840,283; 5,866,105; 5,874,476; 5,916,545; 5,972,317; and 6,022,549. Such prior art topical applications have been largely unsuccessful because the nail is a difficult barrier for anti-fungal compounds to penetrate. To be effective a topical treatment for onychomycosis should exhibit a powerful potency for pathogens. It must also be permeable through the nail barrier, and safe for patient use. There exists a need in the art for a topical application that combines these traits in high degree.

Members of the class of organo-boron compounds have long been known to exhibit biocidal activity. Yet, none of the prior art teachings on treatment of onychomycosis discloses use of compositions containing an organo-boron compound for this purpose, or employs a composition that contains an organo-boron compound as a constituent.

U.S. Pat. No. 3,189,637 to Bengelsdorf et al. describes cycloalkenyl glycol boric acid esters including 2,2'-(alkyldioxy)bis-(alkyl-1,3,2-dioxaborinane) derivatives having utility in a variety of applications, including fungicides.

U.S. Pat. No. 3,877,890 to Maisey et al. describes biocide compositions for controlling and preventing the growth of micro-organisms in jet fuel. The organo-boron compounds of the Maisey et al. patent do not include the dioxaborinane genus of the present invention.

U.S. Pat. No. 4,718,919 to DeLue et al. discloses an anti-icing and biocidal and fungicidal fuel additive including the preferred species of the present invention in combination with an ethylene glycol monoalkylether.

U.S. Pat. No. 4,742,044 to Boden discloses 1,3,2-dioxaborinane derivatives useful in augmenting or enhancing the aroma of perfume compositions, and perfumed articles.

In none of the references describing dioxaborinane compounds is a use for treatment of onychomycosis disclosed or suggested.

The safety and non-toxicity of organo-boron compounds has been questioned.

One reference, "*Sax's Dangerous Properties of Industrial Materials*", Tenth Edition, John Wiley & Sons, New York, 2000, P.546, reports that the "Safety Profile" of "Boron Compounds" is "very toxic", and that "Boron Compounds are therefore considered an industrial poison."

On the other hand, an article entitled, "Recherces Parmacologiques Sur Les Derives Organiques Du Bore", *Therapie* (Paris) 15, 791–802 (1960), discusses the toxicity of the compound 2-(p-tolyl)-(5-methyl, 5-propyl)-1,3,2,-dioxiborinane (termed I.S. 813). When tested for use as a possible sedative, it was found that the toxicity of I.S. 813 was very low. Finally, a fuel additive Biobor® JF containing a combination of 2,2'-(1-methyltrimethylenedioxy)bis-(4-methyl-1,3,2-dioxaborinane) and 2,2'-oxybis(4,4,6-trimethyl-1,3,2-dioxaborinane) with naphtha is sold commercially by Hammonds Fuel Additive Inc., Houston, Tex. The material safety data sheet for this combination identifies as a hazard "Skin Contact: May cause slight to mild irritation. Prolonged or repeated contact may dry the skin and lead to irritation (i.e. dermatitis)".

There remains a need in the art for a topical application which can be safely applied to nails of fingers and toes, and which exhibits in combination permeability and potency for pathogens required to effectively cure, or prevent the spread of onychomycosis.

SUMMARY OF THE INVENTION

The present invention provides a topical composition for treatment of nail infections. The composition comprises, as an active ingredient, at least one species selected from the group consisting of 2,2'-(alkyldioxy)bis-(alkyl-1,3,2-dioxaborinane) and 2,2'-oxybis(alkyl-1,3,2-dioxaborinane). More specifically, the composition comprises, as an active ingredient, at least one member selected from the group consisting of 2,2'-(1-methyltrimethylenedioxy)bis-(4-methyl-1,3,2-dioxaborinane) and 2,2'-oxybis(4,4,6-trimethyl-1,3,2-dioxaborinane). The invention also comprises a method of treating onychomycosis by topical application of a composition containing, as an active ingredient, at least one member selected from the group consisting of 2,2'-(1-methyltrimethylenedioxy)bis-(4-methyl-1,3,2-dioxaborinane) and 2,2'-oxybis(4,4,6-trimethyl-1,3,2-dioxaborinane).

The compositions and method of the invention provide a unique means for treating onychomycosis. Advantageously, such means provides, in combination, certain characteristics, including safety, effectiveness, convenience, and freedom from toxicity, which have been unavailable heretofore. Through in vitro microbiological tests it is now found that a topical formulation containing as active ingredient at least one member selected from the group consisting of 2,2'-(1-methyltrimethylenedioxy)bis-(4-methyl-1,3,2-dioxaborinane) and 2,2'-oxybis(4,4,6-trimethyl-1,3,2-dioxaborinane has powerful potency against *Candida albicans.* That is to say, it is found in accordance with the invention, that active constituents of certain compositions effectively kill the most common pathogen causing onychomycosis. It is also found by in vivo tests on a volunteer that formulations of the invention achieve efficacy in the treatment of onychomycosis without skin irritation or noticeable side effects. One formulation is conveniently applied nightly in a petroleum jelly or mineral oil base. Dilute compositions of the active compounds in alcohol or acetone base has the ability to deliver concentrated active ingredient as the solvent evaporates. Another formulation is conveniently applied once per week in a cellulose acetate lacquer base. Both formulations are effective in curing the onychomycosis without skin irritation and evident side effects.

DETAILED DESCRIPTION OF THE INVENTION

In accordance with the present invention, there is provided a topical composition for treatment of nail infections. Generally stated, the composition comprises, as an active ingredient, at least one species selected from the group consisting of 2,2'-(alkyldioxy)bis-(alkyl-1,3,2-dioxaborinane) and 2,2'-oxybis(alkyl-1,3,2-dioxaborinane). The active ingredient in one composition of the invention has the following general formula:

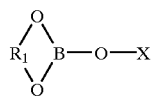

where $R_1$ is a primary, or secondary alkyl group having from 3 to 20 carbon atoms, X represents

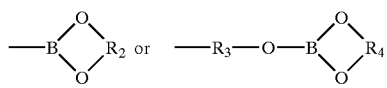

and where $R_2$, $R_3$ and $R_4$ are defined the same as $R_1$ above and may be the same or different primary, or secondary alkyl groups.

More specifically, the composition comprises, as an active ingredient, at least one member selected from the group consisting of 2,2'-(1-methyltrimethylenedioxy)bis-(4-methyl-1,3,2-dioxaborinane) and 2,2'-oxybis(4,4,6-trimethyl-1,3,2-dioxaborinane).

The synthesis of 2,2'-(alkyldioxy)bis-(alkyl-1,3,2-dioxaborinane) and 2,2'-oxybis(alkyl-1,3,2-dioxaborinane) derivatives has been described in U.S. Pat. No. 2,741,548, which description is hereby incorporated by reference; but only to the extent it is not incompatible herewith. Example 2 of U.S. Pat. No. 2,741,548 expressly describes the synthesis of 2,2'-oxybis(4,4,6-trimethyl-1,3,2-dioxaborinane).

It is now found by in vitro microbiological tests that a topical formulation containing as active ingredient at least one member selected from the group consisting of 2,2'-(1-methyltrimethylenedioxy)bis-(4-methyl-1,3,2-dioxaborinane) and 2,2'-oxybis(4,4,6-trimethyl-1,3,2-dioxaborinane) is effective against *Candida albicans*. It is also found by in vivo tests on a volunteer that a formulation of the invention is effective in the treatment of onychomycosis without skin irritation or noticeable side effects.

In one embodiment, the composition of the invention contains as an active ingredient at least one member selected from the group consisting of 2,2'-(1-methyltrimethylenedioxy) bis-(4-methyl-1,3,2-dioxaborinane) and 2,2'-oxybis(4,4,6-trimethyl-1,3,2-dioxaborinane) in combination with at least one member selected from the group consisting of white mineral oil, petroleum jelly and paraffin wax or volatile solvent such as alcohol or acetone. The mineral oil, petroleum jelly and paraffin wax help protect the skin against irritation or drying and serve as a reservoir for the active ingredient permitting extended continuous diffusion and penetration into the nail. The volatile solvents provide more concentrated availability of the active ingredient from dilute solutions as the solvent evaporates.

In another embodiment, the composition of the invention contains as an active ingredient at least one member selected from the group consisting of 2,2'-(1-methyltrimethylenedioxy) bis-(4-methyl-1,3,2-dioxaborinane) and 2,2'-oxybis(4,4,6-trimethyl-1,3,2-dioxaborinane) in combination with an organic film former. The organic film former serves as a long lasting reservoir for the active ingredient, permitting extended continuous diffusion and penetration into the nail. Many suitable film-forming polymers are known. Among those film formers considered to be suitable are polymers and copolymers of vinyl acetate, polymethyl methacrylate, polyvinyl butyral, polyvinyl pyrrolidone, cellulose acetate, and cellulose butyrate.

In yet another embodiment, the composition of the invention contains as an active ingredient at least one member selected from the group consisting of 2,2'-(1-methyltrimethylenedioxy)bis-(4-methyl-1,3,2-dioxaborinane) and 2,2'-oxybis(4,4,6-trimethyl-1,3,2-dioxaborinane) in combination with a penetration enhancer. As used herein, the term "penetration enhancer" means a chemical compound that increases the permeability of the skin to a drug. Several different penetration enhancers have been reported, including dimethyl sulfoxide, and N-methyl-2-pyrrolidone.

The active dioxaborinane ingredient preferably constitutes at least about 0.1 wt. % of a composition of the invention. More preferably, the dioxaborinane ingredient constitutes between about 0.1 wt % and 75 wt % of the composition. Yet more preferably, the dioxaborinane ingredient constitutes between about 0.1 wt % and 50 wt % of the composition. Most preferably, dioxaborinane ingredient constitutes between about 0.1 wt % and 25 wt % of the composition.

The following examples are presented to provide a more complete understanding of the invention. The specific techniques, conditions, materials, proportions and reported data set forth to illustrate the principles and practice of the invention are exemplary and should not be construed as limiting the scope of the invention.

EXAMPLES

Examples 1–15

2,2'-(1-methyltrimethylenedioxy)bis-(4-methyl-1,3,2-dioxaborinane) (hereinafter compound S1) and 2,2'-oxybis (4,4,6-trimethyl-1,3,2-dioxaborinane) (hereinafter compound S2) are each prepared and purified according to the procedures described in U.S. Pat. No. 2,741,548. One or both of the dioxaborinanes is mixed with a sterile U.S.P. grade of white mineral oil in varying proportions as shown in Table I below to form compositions of the invention. The mineral oil is produced by E. R. Squibb & Sons Inc., Princeton, N.J. A control composition consists of the mineral oil alone.

The compositions are evaluated according to an approved surface carrier disinfection test (Official Methods of Analysis of the Association of Official Analytical Chemists protocol 991.47: Hard surface carrier test method). Cultures of *Candida albicans* are grown for 24 hours at room temperature in trypsin soy broth to a density of approximately McFarland standard #10. Sterile glass cylinders (Belco Cat. #2090-S0012) serve as carriers. The carriers are coated with the test composition or the control composition and subsequently submerged in 5 ml of the stock culture and allowed to remain there for 15 minutes.

The carriers are aseptically transferred to sterile, dry Whatman #1 filter paper, and excess droplets of the inoculation medium are removed. The carriers are dried at 37° C. for 40 minutes and then aseptically transferred to 5 ml of trypsin soy broth. They are then sonicated for 10 minutes in as water bath at 25° C. Tubes containing the sonicated carriers are vortexed, and a portion of the medium is placed onto trypsin soy agar plates, and incubated overnight at 37° C. Microbial growth is assessed by counting colonies. The results are presented in Table I.

TABLE I

| Example | Test Compound | Wt. % Of S1/S2 In Mineral Oil | Colonies Of Candida Albicans Observed |
|---|---|---|---|
| Comparative | Mineral oil (control) | 0 | 1203 |
| 1 | S1 | 0.1 | 8 |
| 2 | S1 | 1.0 | 2 |
| 3 | S1 | 10 | 0 |
| 4 | S1 | 25 | 0 |
| 5 | S1 | 50 | 0 |
| 6 | S1 | 75 | 0 |
| 7 | S2 | 0.1 | 11 |
| 8 | S2 | 1.0 | 1 |
| 9 | S2 | 10 | 0 |
| 10 | S2 | 25 | 0 |
| 11 | S2 | 50 | 0 |
| 12 | S2 | 75 | 0 |
| 13 | 25/75 w/w S1/S2 | 25 | 0 |
| 14 | 50/50 w/w S1/S2 | 25 | 0 |
| 15 | 75/25 w/w S1/S2 | 25 | 0 |

The results indicate that each of the formulations in Examples 1–15 of the invention is highly effective in suppressing growth of *Candida albicans* in vitro.

Example 16

A male volunteer 43 years old has onychomycosis of the toenails on both feet. To the toenails of the left foot is applied a mixture consisting of 25 wt % of compounds S1 and S2 in 50/50 w/w proportion, and 75 wt. % of low viscosity petroleum jelly. Selection of this composition is based on the examples of 1–15, which indicates that a 25% loading of either S1 or S2 or combinations thereof completely destroys the fungus. The clinical tests are done to evaluate effectiveness and skin reactions, if any. This mixture is reapplied nightly. To the toenails of the right foot is applied a mixture of 25 wt % of compounds S1 and S2 in 50/50 w/w proportion, 70 wt % acetone and 5 wt % cellulose acetate. This mixture is applied once per week after the previous week's application is removed with acetone. At the end of 6 weeks of treatment, the toenails of each foot have a clear, uninfected zone of 2 mm in width. At the end of 12 weeks of treatment, the clear zone is 4 mm in width. At the end of 20 weeks of treatment, the toenails on both feet are free of infected areas. During the progression of the nail growth a ridge in the nail is seen between the newly grown clear nail which is closely attached to the skin below and the infected nail which is more detached from the skin. No skin irritation is seen on either foot and no side effects are evident.

Example 17

A male volunteer 58 years old has onychomycosis on both feet. At least four toes in each foot are infected. He applies the solution, which has 25% of active ingredients in mineral oil with a 50/50 S1/S2 ratio, to both feet once a day. The application included painting the entire toenail and the cuticle for approximately 3 mm beyond the nail. After 90 days 3 mm of clear infection free nail could be seen. After 125 days, more than three-quarter of the nail is clear, free from infection. The boundary between the infected portion and the clear portion is not smooth and shows structure. In 250 days, the nail is fully-grown, completely free from any infection. No skin irritation is observed.

Example 18

A female volunteer 35 years old has onychomycosis on big toe of right foot near the top one third of the nail. She applies the solution, which has 25% active ingredients in mineral oil with a 50/50 S1/S2 ratio, to both feet once a day. The application included painting the entire toenail and the cuticle for approximately 3 mm beyond the nail. After 90 days the infection on the top third of the nail cleared away with clear nails. The treatment is continued for a total of 180 days at which time no trace of fungus is seen. No skin irritation is observed.

Example 19

A male volunteer 85 years old has onychomycosis on left side of big toe of right feet. He applies the solution, which has 12.5% active ingredients in mineral oil with 50/50 S1/S2 ratio, once a day. The diluted composition is selected to establish the lower limit of anti-fungal activity. He applies the solution for 90 days with clear evidence of destruction of fungus. The ease of fungus destruction is attributed to the closeness of the fungus to the left cuticle, which permitted easy penetration of the solution in spite of its lower concentration of the active ingredient. No irritation of the skin is observed.

Example 20

A female volunteer 50 years old has onychomycosis on big toe and the adjacent toe of left feet. She applies the solution, which has 25% active ingredients in mineral oil with 50/50 S1/S2 ratio, once a day. She applies the solution for 245 days with clear evidence of destruction of fungus on the big toe and the adjacent toe. Onset of clear nail could be seen as early as 92 days when approximately 2 mm of clear nail is observed. Half of the big toe nail is clear in 125 days. No irritation of the skin is observed.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A method for the treatment of nail infections comprising:
    periodically applying to the infected nail a composition comprising:
    a) as active ingredients at least one of a 2,2'-(alkyldioxy) bis-(alkyl-1,3,2-dioxaborinane) and a 2,2'-oxybis (alkyl-1,3,2-dioxaborinane), said active ingredient ranging from about 0.1 wt % to 25 wt % of the composition;
    b) at least one member selected from the group consisting of white mineral oil, petroleum jelly, and paraffin wax;
    for a period sufficient to end the infection.

2. A method for the treatment of nail infections as recited by claim 1 wherein the composition applied comprises as one of the active ingredients 2,2'-(1-methyltrimethylenedioxy)bis-(4-methyl-1,3,2-dioxaborinane) or 2,2'-oxybis(4,4,6-trimethyl-1,3,2-dioxaborinane).

* * * * *